(12) United States Patent
Garbe et al.

(10) Patent No.: US 7,348,409 B2
(45) Date of Patent: Mar. 25, 2008

(54) ANTIMICROBIALLY ACTIVE PEPTIDE

(75) Inventors: Claus Garbe, Tuebingen (DE); Birgit Schittek, Stuttgart (DE)

(73) Assignee: Eberhard-Karls-Universitaet Tuebingen Universitaetskilinikum, Tuebingen (DE)

( * ) Notice: Subject to any disclaimer, the term of this patent is extended or adjusted under 35 U.S.C. 154(b) by 32 days.

(21) Appl. No.: 10/735,481

(22) Filed: Dec. 12, 2003

(65) Prior Publication Data

US 2008/0020976 A1    Jan. 24, 2008

Related U.S. Application Data

(63) Continuation of application No. PCT/EP02/06238, filed on Jun. 7, 2002.

(30) Foreign Application Priority Data

Jun. 13, 2001 (DE) .................. 101 29 983

(51) Int. Cl.
  *C07K 1/00* (2006.01)
  *A61K 38/00* (2006.01)
  *C07H 21/04* (2006.01)
(52) U.S. Cl. ............. 530/350; 530/326; 536/23.4
(58) Field of Classification Search ........... 530/326, 530/350; 536/23.4; 424/184.1, 800
See application file for complete search history.

(56) References Cited

U.S. PATENT DOCUMENTS 5,834,192 A * 11/1998 Akerblom et al. ............. 435/6
6,008,195 A * 12/1999 Selsted ..................... 514/14
6,420,116 B1 * 7/2002 Olsen et al. .................. 435/6

OTHER PUBLICATIONS

Schittek et al (Dermcidin: a novel human antibiotic peptide secreted by sweat glands, Nature Immunology, 2001; 2(12): 1133-1137).*
Thomas E. Creighton, in his book, "Proteins: Structures and Molecular Properties", 1984: 314-315.*
Thomas E. Creighton, in his book "Protein Structure: A Practical Approach", 1989: 184-186.*
Nosoh, Y. et al "Protein Stability and Stabilization through Protein Engineering", 1991(chapter 7, p. 197).*
UniProtKB/Swiss-Prot entry P81605 http://ca.expasy.org/uniprot/P81605 pp. 1-4.*
Cunningham et al, Identification of a survival-promoting peptide in medium conditioned by oxidatively stressed cell lines of nervous system origin, The journal of neuroscience, 1998; 18(18): 7047-60.*
Bowie et al (Science, 1990, 257: 1306-1310).*
Cunningham et al. (2000) "Calreticulin binding and other biological activities of survival peptide Y-P30 including effects of systemic treatment of rats," Experimental Neurology 163:457-468.
Hipfel et al. (2000) "Specifically regulated genes in malignant melanoma tissues identified by subtractive hybridization," British Journal of Cancer 82(6):1149-1157.

* cited by examiner

*Primary Examiner*—Robert A. Zeman
*Assistant Examiner*—Lakia J Tongue
(74) *Attorney, Agent, or Firm*—Knobbe, Martens, Olson & Bear, LLP

(57) ABSTRACT

An antimicrobially active peptide comprises the DCD protein or a fragment of DCD, preferably derived from the C-terminal region.

3 Claims, 5 Drawing Sheets

Fig 1A

5'-UTS →
5'-GACCCTAGAT CCCAAGATCT CCAAGGATTT GGTGGCATAC CCACTCCAGC ACACAGAAGC ATGAGGTTCA
                                                                    start codon exon 1                                    intron 1              exon 2
TGACTCTCCT CTTCCTGACA GCTCTGGCAG GAGCCCTGGT CTGTGCCT ⇑ AT GATCCAGAGG CCGCCTCTGC intron 2            exon 3
CCCAGGATCG GGGAACC ⇑ CTT GCCATGAAGC ATCAGCAGCT CAAAAGGAAA ATGCAGGTGA AGACCCAGGG intron 3               exon 4
TTAGCCAGAC AGGCACCAAA GCCAAGGAAG CAGAGATCCA GCCTTCTGG ⇑ A AAAAGGCCTA GACGGAGCAA intron 4
AAAAAGCTGT GGGGGACTC GGAAAACTAG GAAAAGATGC AGTCGAAGAT CTAGAAAGCG TGGGTAAAGG ⇑ exon 5                                  stop codon
AGCCGTCCAT GACGTTAAAG ACGTCCTTGA CTCAGTACTA TAGCTGTAAG GAGAAGCTGA GAAATGATAC

← 3'-UTS
CCAGGAGCAG CAGGCTTTAC GTTTTCAGCC TAAAACCT

Fig 1B

MRFMTLFLT ALAGALVCAY DPEAASAPGS GNPCHEASAA QKENAGEDPG LARQAPKPRK QRSSLLEKGL
DGAKKAVGGL GKLGKDAVED LESVGKGAVH DVKDVLDSVL

SEQUENCE LISTING

<160> NUMBER OF SEQ ID NOS: 7

<210> SEQ ID NO 1
<211> LENGTH: 110
<212> TYPE: PRT
<213> ORGANISM: Homo sapiens

<400> SEQUENCE: 1

```
Met Arg Phe Met Thr Leu Leu Phe Leu Thr Ala Leu Ala Gly Ala Leu
 1               5                  10                  15

Val Cys Ala Tyr Asp Pro Glu Ala Ala Ser Ala Pro Gly Ser Gly Asn
            20                  25                  30

Pro Cys His Glu Ala Ser Ala Ala Gln Lys Glu Asn Ala Gly Glu Asp
        35                  40                  45

Pro Gly Leu Ala Arg Gln Ala Pro Lys Pro Arg Lys Gln Arg Ser Ser
    50                  55                  60

Leu Leu Glu Lys Gly Leu Asp Gly Ala Lys Lys Ala Val Gly Gly Leu
65                  70                  75                  80

Gly Lys Leu Gly Lys Asp Ala Val Glu Asp Leu Glu Ser Val Gly Lys
                85                  90                  95

Gly Ala Val His Asp Val Lys Asp Val Leu Asp Ser Val Leu
            100                 105                 110
```

<210> SEQ ID NO 2
<211> LENGTH: 48
<212> TYPE: PRT
<213> ORGANISM: Artificial Sequence
<220> FEATURE:
<223> OTHER INFORMATION: synthetic fragment of DCD protein

<400> SEQUENCE: 2

```
Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45
```

<210> SEQ ID NO 3
<211> LENGTH: 47
<212> TYPE: PRT
<213> ORGANISM: Artificial Sequence
<220> FEATURE:
<223> OTHER INFORMATION: synthetic fragment of DCD protein

<400> SEQUENCE: 3

```
Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val
        35                  40                  45
```

<210> SEQ ID NO 4
<211> LENGTH: 30
<212> TYPE: PRT
<213> ORGANISM: Artificial Sequence
<220> FEATURE:
<223> OTHER INFORMATION: synthetic peptide

<400> SEQUENCE: 4

```
Tyr Asp Pro Glu Ala Ala Ser Ala Pro Gly Ser Gly Asn Pro Cys His
 1               5                  10                  15

Glu Ala Ser Ala Ala Gln Lys Glu Asn Ala Gly Glu Asp Pro
            20                  25                  30
```

<210> SEQ ID NO 5
<211> LENGTH: 30
<212> TYPE: PRT
<213> ORGANISM: Artificial Sequence
<220> FEATURE:
<223> OTHER INFORMATION: synthetic peptide

<400> SEQUENCE: 5

```
Asp Pro Tyr Ala Glu Ala Ala Ser Gly Pro Asn Pro Gly Ser Lys Ser
 1               5                  10                  15

His Glu Ser Ala Gln Ala Glu Asn Cys Gly Ala Asp Pro Glu
            20                  25                  30
```

<210> SEQ ID NO 6
<211> LENGTH: 458
<212> TYPE: DNA
<213> ORGANISM: Homo Sapiens

<400> SEQUENCE: 6

```
gaccctagat cccaagatct ccaaggattt ggtggcatac ccactccagc acacagaagc    60
```

```
                                         -continued atgaggttca tgactctcct cttcctgaca gctctggcag gagccctggt ctgtgcctat    120
gatccagagg ccgcctctgc cccaggatcg gggaacccct tgccatgaagc atcagcagct    180 caaaaggaaa atgcaggtga agacccaggg ttagccagac aggcaccaaa gccaaggaag    240
cagagatcca gccttctgga aaaaggccta gacggagcaa aaaaagctgt gggggggactc   300 ggaaaactag gaaaagatgc agtcgaagat ctagaaagcg tgggtaaagg agccgtccat    360
gacgttaaag acgtccttga ctcagtacta tagctgtaag gagaagctga gaaatgatac    420
ccaggagcag caggctttac gttttcagcc taaaacct                            458

<210> SEQ ID NO 7
<211> LENGTH: 24
<212> TYPE: PRT
<213> ORGANISM: Artificial Sequence
<220> FEATURE:
<223> OTHER INFORMATION: synthetic peptide

<400> SEQUENCE: 7

Lys Glu Asn Ala Gly Glu Asp Pro Gly Leu Ala Arg Gln Ala Pro Lys
  1               5                  10                  15

Pro Arg Lys Gln Arg Ser Ser Leu
            20
```

ANTIMICROBIALLY ACTIVE PEPTIDE

CROSS-REFERENCES TO RELATED APPLICATIONS

This application is a continuation of copending international patent application PCT/EP02/06238 filed on Jun. 7, 2002 and designating the U.S., which was not published under PCT Article 21(2) in English, and claims priority of German patent application DE 101 29 983.4 filed on Jun. 13, 2001, which is incorporated herein by reference.

BACKGROUND OF THE INVENTION

1. Field of the Invention

The present invention relates to an antimicrobially active peptide and to its preparation and to a method for protecting and/or treating human skin against microorganisms.

2. Description of the Related Art

The epithelial tissue of mammals represents an important barrier to the surroundings and provides a first line of defense against invading microorganisms. In particular, antimicrobial peptides, of which there are many in the epidermis, participate in the defense system. They control microbial growth in the first hours after epithelial injury and during wound healing. In particular, they can be found in some inflammatory disorders of the skin.

To date, two classes of antimicrobial peptides have been discovered in mammalian skin, the cathelicidins and the β-defensins. They are induced in human creatinocytes after induction by inflammatory stimuli and act primarily as a response to injuries and not within the framework of a constant modulation of the epithelial defense mechanism.

Whereas, for example, cathelicidin PR-39 is a component of wound fluid and appears to be involved in wound healing, cathelicidin LL-37 is expressed in human skin creatinocytes at inflammatory sites in various diseases.

Defensins are small cationic peptides having a molecular weight of from 3 to 5 kDa, and they have an antibacterial and antimycotic effect. The α-defensins HD1-4 are expressed for example in human neutrophils which accumulate in infected tissue regions. The α-defensins HD-5 and HD-6 are, by contrast, produced by epithelial granulocytes.

In general, antimicrobial peptides are endogenous, gene-encoded peptides with particular importance for the early phase of defense against microbial pathogens. They can be detected within minutes to hours after the first contact with the pathogen.

However, known antimicrobial peptides do not act against all microbial pathogens in the same way; for example defensins have only an inadequate effect on infections with *S. aureus*, an important cause of skin infections, especially associated with atopic dermatitis.

Antibiotics are also employed preventively or curatively for controlling pathogenic microorganisms, these being substances of microbiological origin which inhibit the growth of or even kill other microorganisms. In contrast to the above-mentioned cathelicidins and defensins, antibiotics usually have selective activity. Many microorganisms have a natural insensitivity to an antibiotic, but they may also develop this so-called antibiotic resistance during growth in the presence of antibiotics.

Mutation and selection processes, and the development of resistances are causing problems increasingly frequently, not only in clinical routine but also in the manufacture of medicaments and cosmetics, with microbial pathogens which can be controlled inefficiently or not at all.

Against this background, there is a continuing need for novel antimicrobially active agents which can be employed preventively or curatively.

Against this background, an object underlying the present invention is to provide a further antimicrobially active peptide and indicate a way for producing it.

SUMMARY OF THE INVENTION

This object is achieved according to the invention by an antimicrobially active peptide which comprises the DCD protein comprising the sequence SEQ ID No: 1 from the appended sequence listing, or a DCD fragment preferably derived from the C-terminal region.

This object underlying the invention is completely achieved in this way.

This is because the inventors of the present application have been able to identify, in a skin cDNA library, a gene which they have called dermcidin (hereinafter: DCD). The gene consists of five exons and four introns and is located on chromosome 12q13 between the D12S1896 and D12S1632 markers (lod score 14.11).

DCD has a very restrictive expression pattern because the gene is expressed only in human skin and was undetectable neither in 50 analyzed human tissues of various origins nor in human fibroblasts, keratinocytes, melanocytes or melanoma cell lines.

The gene encodes a peptide which belongs to a new class of antimicrobial proteins and displays broad-spectrum activity. The peptide is specifically expressed in sweat glands, secreted in the sweat and transported to the epidermal surface. In sweat, it is proteolytically processed to a peptide which displays a dose-dependent antimicrobial effect on a large number of pathogenic microorganisms. The inventors have been able to show, using an antimicrobial assay, that the DCD protein is toxic for *Escherichia coli, Enterococcus faecalis, Staphylococcus aureus* and *Candida albicans*.

Until the present invention, no antimicrobial peptides had been discovered in human sweat. From the finding of DCD, and from the experimental demonstration that DCD and fragments of DCD have antimicrobial effects, the inventors of the present application conclude that sweat plays a role in regulation of the human skin flora and that DCD has therapeutic importance for the treatment of disorders of the skin. The amount of DCD present in sweat is 1-10 µg/ml, and exactly this concentration range exhibits an antimicrobial effect on the abovementioned pathogens in the experimental approach.

Comparison with GenBank surprisingly revealed that the cDNA sequence of DCD has been published by Akerblom et al. as "human cachexia associated protein" (HCAP). The authors describe in U.S. Pat. No. 5,834,192 the identification and isolation of HCAP from a breast tumor library and propose the therapeutic use of HCAP and of the encoding gene within the framework of treatment of tumor-induced cachexia. An antimicrobial effect of HCAP is not disclosed.

It is of interest that a short segment in the N-terminal region of DCD—amino acid residues 20-49—shows 96 percent homology with a "survival promoting peptide" called Y—P30; see Cunningham et al.: "Calreticulin Binding and Other Biological Activities of Survival Peptide Y—P30 Including Effects of Systemic Treatment of Rats", Experimental Neurology 163, 254-268 (2000).

Y—P30 was purified from oxidatively stressed neural cell lines and apparently has a survival-favoring effect on neurons, because direct application of this peptide to lesions of the rat cerebral cortex permits the survival of neurons which normally degenerate after a cortical lesion. The authors propose that Y—P30 is secreted by neural cells for the purpose of cytoprotection as a response to stress.

It is preferred, in a further development of the invention, for the fragment to comprise a maximum of 50 amino acid residues from the C-terminal region of DCD, preferably either the amino acid residues 63-110 (SEQ ID No: 2) or amino acid residues 63-109 (SEQ ID No: 3).

It has emerged that these fragments have an outstanding antimicrobial effect, in particular on the abovementioned pathogens. Since these fragments are also distinctly shorter than the mature DCD protein, which comprises 110 amino acid residues, with the first 19 N-terminal amino acid residues being a signal peptide, they can be prepared more easily and less expensively both by chemical synthesis and biotechnologically than the mature DCD protein. However, the smaller size of the fragments compared with the mature DCD protein also has, besides the possibility of easier and less expensive preparation, the further advantage that shorter fragments are ordinarily more stable than longer ones, so that both manipulation and administration of the fragments is simpler than with the mature protein and thus displays further advantages.

Also a further truncation of the two fragments SEQ ID No: 2 and SEQ ID No: 3 at the N-terminal end impair the antimicrobial effect, whereas the inventors have been able to establish that a truncation to the 31 C-terminal amino acid residues of DCD leads to a peptide which has no appreciable antimicrobial effect.

It is further preferred, compared with the corresponding position in the mature DCD protein, for at least one amino acid to be exchanged for an amino acid of the same group.

It is known that the so-called proteinogenic amino acids can be divided into four groups, and that replacement of one amino acid in a peptide by an amino acid of the same group frequently alters the function of the peptide only slightly or not at all. Such an amino acid exchange may be worthwhile in particular in relation to a chemical synthesis or a biotechnological production if the corresponding peptide can, by reason of the exchange, be produced in a higher yield, the antimicrobial effect being retained owing to the exchange within one group.

It may be mentioned, only for the sake of completeness, that the amino acid groups are characterized as follows: I. amino acids with neutral and hydrophobic (nonpolar) side chains, II. amino acids with neutral and hydrophilic (polar) side chains, III. amino acids with acidic and hydrophilic (polar) side chains and IV. amino acids with basic and hydrophilic (polar) side chains.

A further object of the invention is a peptide which comprises an amino acid sequence homologous to the novel peptide and shows a comparable antimicrobial effect.

A homologous peptide means within the scope of the present invention a peptide which has arisen by divergent evolution from a common precursor of DCD and displays great correspondence not only in the primary structure but also in the secondary structure and tertiary structure, is produced in a biologically comparable way, and has a comparable function. This is because, as the inventors have been able to show that DCD protein which is expressed in human sweat glands and is secreted and processed, and C-terminal fragments of the DCD protein, respectively, some of which occur naturally in human sweat, display an antimicrobial effect, it is possible to find corresponding homologous peptides in other mammals without difficulty. Starting from the surprising finding that at least one antibacterially active peptide is present in human sweat, the steps for finding homologous peptides also in other mammals are prefigured to such an extent that they are included in the present invention.

In a further development, it is preferred for the peptide to have at least one post-translational modification.

Post-translational modification means within the scope of the present application in particular the attachment of prosthetic groups (for example glycosylation) and modification of amino acid residues (for example alkylation). Thus, in the general sense, a post-translational modification means any difference between the functional peptide employed according to the invention and the linear sequence of the unmodified amino acid residues.

Such post-translational modifications may serve the stability of the peptide or an increased biological activity, but may also be attributable to a biotechnological production. Thus, production of peptides in prokaryotic cells leads to a reduced form of the peptide, whereas production in eukaryotic cells may lead to a glycosylated peptide. It may additionally be worthwhile to provide at least one of the amino acids of the peptide with a protective group in order to protect the peptide from attack by exopeptidases.

It is preferred in one embodiment for the peptide to be connected to a further peptide or protein to give a fusion protein, in which case the further peptide or protein is preferably selected from the group: signal peptide, reporter protein, histidine tags, antigenic determinants etc.

If peptides are synthesized as fusion peptides, the preparation and purification of the peptides according to the invention may be facilitated. In this case, sequences encoding amino acid segments or domains of known proteins are fused onto nucleic acids encoding the peptides of the invention, so that a continuous peptide is generated on expression. Examples of such fused-on amino acid segments are, for example, the histidine tags, by means of which the expressed fusion proteins can be purified on nickel chelate acids, or antigenic determinants, which permit the peptides to be purified on suitable antibody affinity columns. Signal peptides may ensure reliable exportation of the generated peptide, while reporter proteins, such as, for example, eGFP (enhanced green fluorescent protein) makes optical detection of the generated peptide possible.

As already mentioned, the novel peptide can be prepared by chemical synthesis, also called Merrifield synthesis, or by techniques of molecular biology.

Against this background, a further object of the invention is a nucleic acid molecule comprising a sequence segment encoding a peptide according to the invention, to an expression vector comprising such a nucleic acid molecule and, where appropriate, control sequences, in particular for replication, transcription and/or translation, and to a host cell which is transfected or transformed with the expression vector.

Since the amino acid sequence of the peptide of the invention is known, a corresponding nucleic acid sequence can be deduced with the aid of the genetic code, it being possible to use optimized codons for different hosts (bacteria, yeast, mammalian cells). However, the codon choice evident from FIG. 1 is preferred.

Preparation of a peptide according to the invention by nucleic acid expression has the advantage that the peptide can be prepared in virtually unlimited quantities. However, the peptide can also in addition be modified in a simple manner by, specifically, modifying the corresponding coding sequence at the nucleic acid level in order thus to bring about an amino acid exchange. At the nucleic acid level it is also possible to produce probes in order to search for homologous peptides in sweat glands of other mammalian cells.

As already mentioned, a further object of the invention is a method for protecting and/or treating human skin against microorganisms, comprising the step of administering a peptide according to the invention onto human skin.

Since DCD is expressed in sweat glands, the inventors have realized that the peptides according to the invention are particularly suitable for the protection and treatment in particular of human skin.

Against this background, another object of the invention is a pharmaceutical or cosmetic composition which comprises as active ingredient a peptide of the invention in an antimicrobially effective amount, preferably in the region of 1-50 µg/ml.

It will be appreciated that the features mentioned above and yet to be explained hereinafter can be used not only in the combinations indicated in each case but also in other combinations or alone without leaving the scope of the present invention.

BRIEF DESCRIPTION OF THE DRAWINGS

Further advantages are evident from the following description in connection with the drawings. These show:

FIG. 1 in FIG. 1A the DNA sequence for DCD (SEQ ID NO: 6) and in FIG. 1B the amino acid sequence (SEQ ID NO: 1);

DETAILED DESCRIPTION OF THE PREFERRED EMBODIMENT

Example 1

Figure 2:
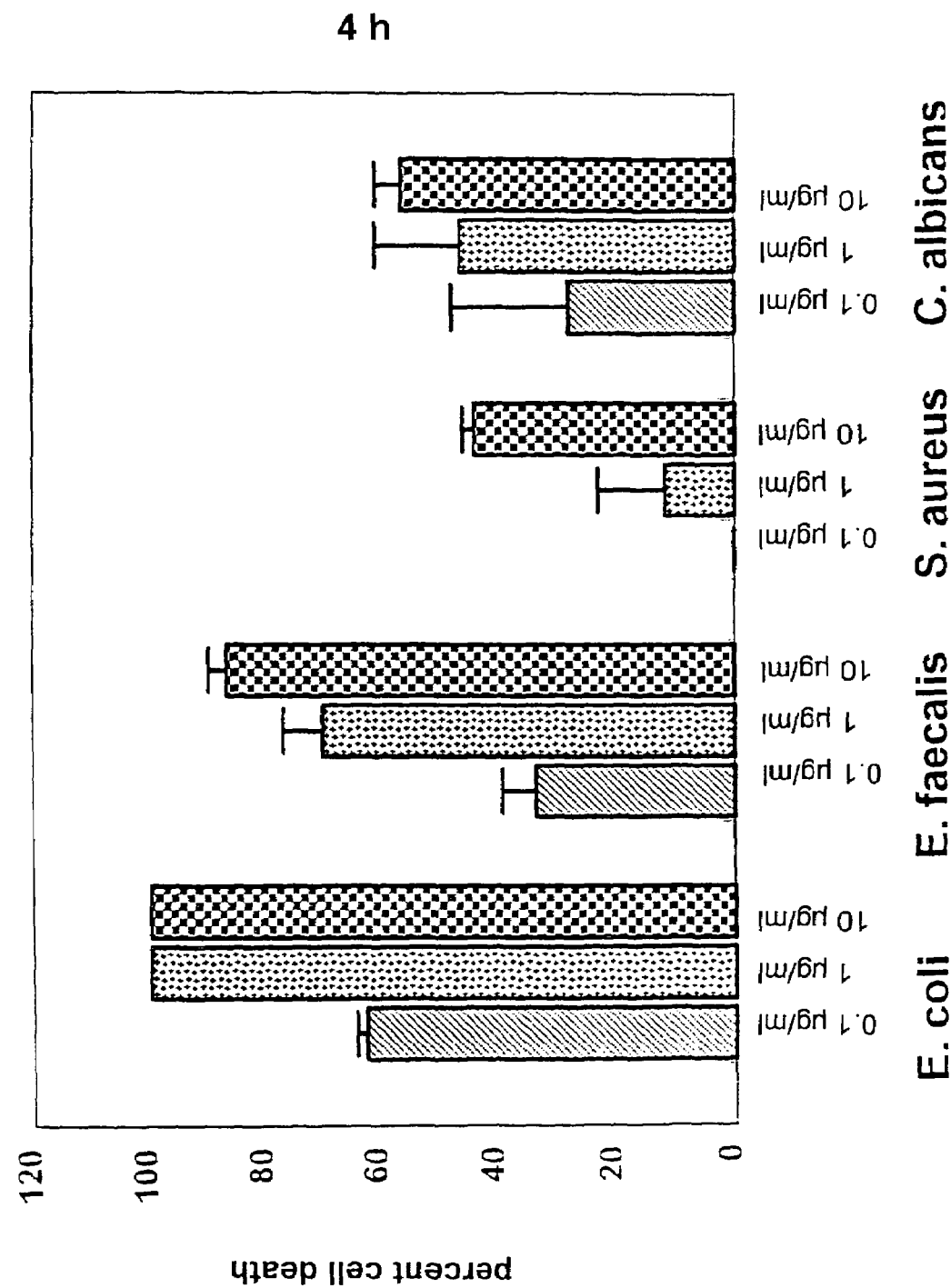
FIG. 2 in a bar diagram the quantity-dependent antimicrobial effect of the DCD-eGFP fusion protein on various microbial pathogens with an incubation time of 4 h. The left-hand bar corresponds in each case to an amount of 0.1 µg/ml peptide the middle bar to an amount of 1 µg/ml and the right-hand bar to an amount of 10 µg/ml.

Isolation of the DCD cDNA and Determination of the Genomic Sequence

In the screening of a subtractive cDNA library of primary melanoma tissue and benign melanocyte nevus tissue using cDNA arrays, a clone which was overexpressed in the nevus tissue compared with the melanoma tissue and which, at the time of isolation, had no sequence homology with a gene published in GenBank was isolated; Hipfel et al., "Specifically Regulated Genes in Malignant Melanoma Tissues Identified by Subtractive Hybridization", British Journal of Cancer 82, 1149-1157 (2000). The clone referred to as clone 8 in the publication therein was subsequently called dermicidin (DCD).

The full length of the DCD cDNA was determined by sequencing overlapping PCR products, and it is 458 bp with an open reading frame of 330 bp, which codes for 110 amino acid residues. The gene consists of five exons and four introns and is expressed as a single transcript.

FIG. 1A indicates the genomic sequence of the DCD gene for the five exons, and FIG. 1B shows the peptide sequence which is to be found as SEQ ID No: 1 in the sequence listing. The first 19 N-terminal amino acid residues of the 110 amino acid residues represent a signal peptide.

DCD was assigned to chromosome 12q13 between the D12S1896 and D12S1632 markers (lod score 14.11). The molecular weight of the unmodified protein is 11.2 kDa including the signal peptide and 9.5 kDa without the signal peptide.

Example 2

Detection of DCD in Various Tissue Samples

The DCD expression profile was determined by testing by the dot-blot technique RNA from fifty different tissues and development stages, using labeled DCD cDNA as probe. No detectable signal was found in any of the fifty samples.

In order to analyze whether the DCD gene is expressed to only a very small extent in human tissue or human cell lines, an RT-PCR was carried out for the DCD gene (Clontech MTC Panels). It emerged that DCD is strongly expressed in human skin, human melanocytic nevus tissue and melanoma tissue, but that DCD is not expressed in the other sixteen human tissues analyzed or in fetal and various tumor tissues. In addition, no amplification products were found after an RT-PCR with forty cycles in different parts of the human digestive system and in various tumor cell lines either.

It can be inferred from these results that DCD expression is confined to cells in the skin.

The cell type which expresses the DCD gene was determined by means of in situ hybridization, immunohistochemistry, immunofluorescence and immunoelectron microscopy.

The in situ hybridization revealed that the gene is expressed in eccrine sweat glands within the dermis of the human skin. No signals were detected on use of a sense probe for DCD as negative control.

A DCD antiserum was raised in rabbits for the immunohistology, using as antigenic determinant the peptide KENAGEDPGLARQAPKPRKQRSSL (SEQ ID NO: 7) which was coupled to KLH for T-cell stimulation. The antigenic determinant corresponds to the amino acid sequence 42-65 from the DCD peptide. It emerged from the investigated skin sections that there was intense staining of the eccrine sweat glands, but no expression on other skin cell types.

For the immunofluorescence, the sections were stained with the polyclonal anti-DCD antiserum mentioned in the previous paragraph, and then incubated with an donkey anti-rabbit antibody labeled with Cy5 (Dianova, Hamburg). The myoepithelial cells of the secreting section of the eccrine sweat glands were then labeled with a monoclonal anti-actin antibody (Enzo Diagnostics, marketed by Loxo, Dossenheim, Germany), stained with a Cy3-labeled donkey anti-mouse antibody (Dianova, Hamburg) and all nuclei were stained with YOPRO (Molecular Probes, Leiden, the Netherlands). The sections were analyzed using a confocal laser scanning microscope (Leica TCS SP, Leica Microsystems, Benzheim) with 250× magnification.

A strong immunofluorescence staining was observable in the secreting sections of the eccrine sweat glands. Only a weak and greatly reduced staining was observable in secreting sections of apocrine sweat glands.

Finally, it was possible by immunoelectron microscopy to localize the DCD protein in the dark mucus-secreting cells of the secreting section of eccrine sweat glands. Ultrastructurally DCD was localized within the Golgi apparatus and in the secreting granules.

In a Western blot analysis of human sweat, three major protein bands were detected at approximately 17, 20 and 24 kDa using the abovementioned antiserum (amino acid residues 42-65 of DCD). The protein with the higher molecular weight was detected only in some sweat samples, whereas the other two bands are detected even when sweat is analyzed under non-reducing conditions.

It is evident from these data that full-length DCD is expressed in the dark mucus-secreting cells in sweat glands and is transported from the Golgi apparatus via secreting granules to the luminal surface of the cells, where the protein is secreted into the duct. It was possible to calculate from the Western blot analysis that the quantity of full-length DCD protein in sweat is between 1 and 10 µg/ml. The three major protein bands detected in the sweat and reacting with the DCD antiserum appear to be forms with different post-translational modifications of the complete DCD protein.

Example 3

Construction, Expression and Characterization of a DCD-eGFP Fusion Protein

The complete DCD cDNA without stop codon was cloned in frame into the pEGFP vector (Clontech, Heidelberg) 5' to the eGFP gene, thus generating a fusion gene called DCD-eGFP. The correct sequence was confirmed by sequence analysis.

SKMEL28 melanoma cells (PNAS 73, 3278-3282 (1976)) were transfected with 1-2 µg of DCD-eGFP or eGFP alone using Fugen (Roche, Mannheim) and cultivated in RPMI with 10% FCS.

After 48 hours, 500 µm/ml G418 (Calbiochem, Schwalbach) were added to the medium, and the amount of G418 was changed to 1 mg/ml after one week. The cells were kept in selection medium and cloned by limiting dilution. A stable clone from each transfection was used for further analysis. Cell lysates of the two clones ($5-7\times10^6$ cells) were prepared by incubating the cells in 1.2 ml of lysis buffer (PBS with 0.5% Triton X-100, 5 mM EDTA, 0.1 mM PMSF, 10 µM pepstatin A, 10 µM leupeptin, 25 µg/ml aprotinin) for 30 minutes. The lysates were separated from the nuclei by centrifugation at 12 000 rpm for 20 min. The supernatants, free of FCS, G418 and penicillin/streptomycin, of transfected and untransfected SKMEL28 control cells were concentrated and desalted by ultrafiltration using an Amicon filtration cell (10,000 Da) and Amicon Centricon Plus-20 columns with a Biomax-5 membrane (5,000 Da).

Western blot with the antiserum described in example 2 revealed in the cell lysate a fusion protein of 44 kDa and in the concentrated supernatant two proteins of 33 and 44 kDa. The eGFP protein (24 kDa) was found only in the cell lysate and not in the supernatant.

The amino acid composition of DCD was investigated further by incubating the concentrated supernatants with various proteases (Sigma, Taufkirchen) and loading the proteins onto an 11% SDS gel. Western blots were then carried out with an anti-GFP antibody.

The proteases trypsin (300 µg/ml) and chymotrypsin (300 µg/ml) were incubated in 10 mM Tris-HCL, pH 8.0, containing 2 mM $CaCl_2$ at 37° C. for 1 h. Two µl of ArgC endoproteinase (100 µg/ml) were incubated in a buffer which contained 0.1 M Tris-HCl pH 8.0, 8 mM $CaCl_2$, 50 mM DDT and 5 mM EDTA at 34° C. for 2 h.

The protease digestion of the fusion protein showed that DCD-eGFP is degraded to the size of the GFP protein by the proteases trypsin and chymotrypsin. The ArgC endoprotease, which cuts at the C-terminal end of arginine residues, was unable to degrade the fusion protein, although three potential cleavage sites are present in the full-length mature protein (without signal peptide); see FIG. 1b, where an arginine residue (R) is evident in positions 53, 59 and 62 of the mature protein.

It is evident from these results that the cleavage site for ArgC is not present in the fusion protein. Since, moreover, the fusion protein cannot be recognized by the DCD antiserum from example 2 in the Western blot, it is evident that DCD is processed proteolytically in order to yield a truncated peptide which lacks at least the first 47 amino acid residues of the secreted mature protein.

In other words, a peptide containing the last 48 C-terminal amino acid residues (62-110) or less is generated from the full-length DCD protein in sweat. This peptide lacks part of the antigenic determinant used for the immunization, and it is therefore undetectable by the antiserum from example 2. Although eccrine sweat glands can be stained with the antiserum, a stable DCD protein having the antigenic region was to be found only in some sweat samples. The DCD-eGFP fusion protein was also undetectable with the antiserum in the concentrated supernatant.

Example 4

Antimicrobial Tests

In order to elucidate the property of DCD and of the truncated DCD peptides further, inter alia the antimicrobial effect of the DCD-eGFP fusion protein, of a synthetically prepared peptide having the 48 C-terminal amino acid residues of DCD (SEQ ID No: 2) and of a peptide (SEQ ID No: 3) derived from HPLC fractionation of human sweat, was investigated. This latter peptide had a mass of 4702 daltons and corresponds to the sequence SEQ ID No: 2 apart from the C-terminal leucine. This peptide isolated from sweat is listed as SEQ ID No: 3 in the sequence listing.

The antimicrobial effect of said peptides was carried out by a CFU test (test for colony-forming units) as described for the defensins by Valore et al., "Human Beta-Defensin-1: An Antimicrobial Peptide of Urogenital Tissues", J Clin Invest 101, 1633-1642 (1998).

The test of the novel peptides was carried out with *Escherichia coli, Staphylococcus aureus, Enterococcus faecalis* and *Candida albicans*. *E. coli* was incubated in LB medium, *E. faecalis* and *S. aureus* in Columbia medium (Difko, BD Heidelberg) and *C. albicans* in casein hydrolysate medium (Merck, Darmstadt). The amounts of bacteria and yeasts were determined by photometry. The bacterial strains were incubated to an optical density of 0.7-0.4 at 600 nm and the yeast was incubated to an optical density of 0.4-0.6 at 450 nm. The amount of the organisms was determined by plating various dilutions as follows: an OD of 1 at 600 nm is equivalent to $8.2\times10^9$/ml for *E. coli*, 1.9×

$10^{10}$/ml for *S. aureus* and $9.0 \times 10^9$/ml for *E. faecalis*, and an OD of 1 at 459 nm is equivalent to $1.4 \times 10^8$/ml for *C. albicans*.

The cells were washed twice with 10 mM sodium phosphate buffer (pH 7.4) and diluted to $2-3 \times 10^7$ cells/ml (*E. coli, E. faecalis*), $5.7 \times 10^7$ cells/ml (*S. aureus*) or $5 \times 10^5$ cells/ml (*C. albicans*) in phosphate buffer.

The cells were incubated with various amounts of the peptides in 200 μl of sodium phosphate buffer at 37° C. for 3 h, 4 h or overnight (21-24 h). The cells were diluted 1:10 to 1:100 for the bacteria and 1:500 to 1:5000 for the yeast, and 50 μl, 100 μl and 200 μl were plated on appropriate agar plates. The plates were incubated at 37° C. overnight, and the number of colonies was counted. The antimicrobial effect of the peptides has been stated as percentage of killed cells: [1−(cell survival after incubation with the peptide)/(cell survival after control incubation)]×100.

In addition to the fusion protein and the peptides of SEQ ID No: 2 and SEQ ID No: 3, the antimicrobial effect of eGFP, Y—P30 (YDPEAASAPGSGNPCH-EASAAQKENAGEDP (SEQ ID NO: 4), this corresponds to the Y—P30 mentioned in the description, but with the amino acid K replacing C in position 23 in order to obtain 100% homology to the amino acid segment 19-39 of DCD), and a control peptide DPI (DPYAEAASGPNPGSKSH-ESAQAENCGADPE, (SEQ ID NO: 5)) was tested.

Whereas no appreciable antimicrobial effect was detectable for eGFP, Y—P30 and DPI, a quantity-dependent antimicrobial effect was shown by the DCD-eGFP fusion protein and by the peptides of SEQ ID No: 2 and SEQ ID No: 3, as is evident from FIGS. 2 to 5.

FIG. 2 shows the antimicrobial effect on the four pathogens mentioned by the DCD-eGFP fusion protein (from concentrated supernatant) with an incubation time of 4 h. The left-hand bar corresponds in each case to an amount of 0.1 μg/ml peptide, the middle bar to an amount of 1 μg/ml and the right-hand bar to an amount of 10 μg/ml.

Figure 3:
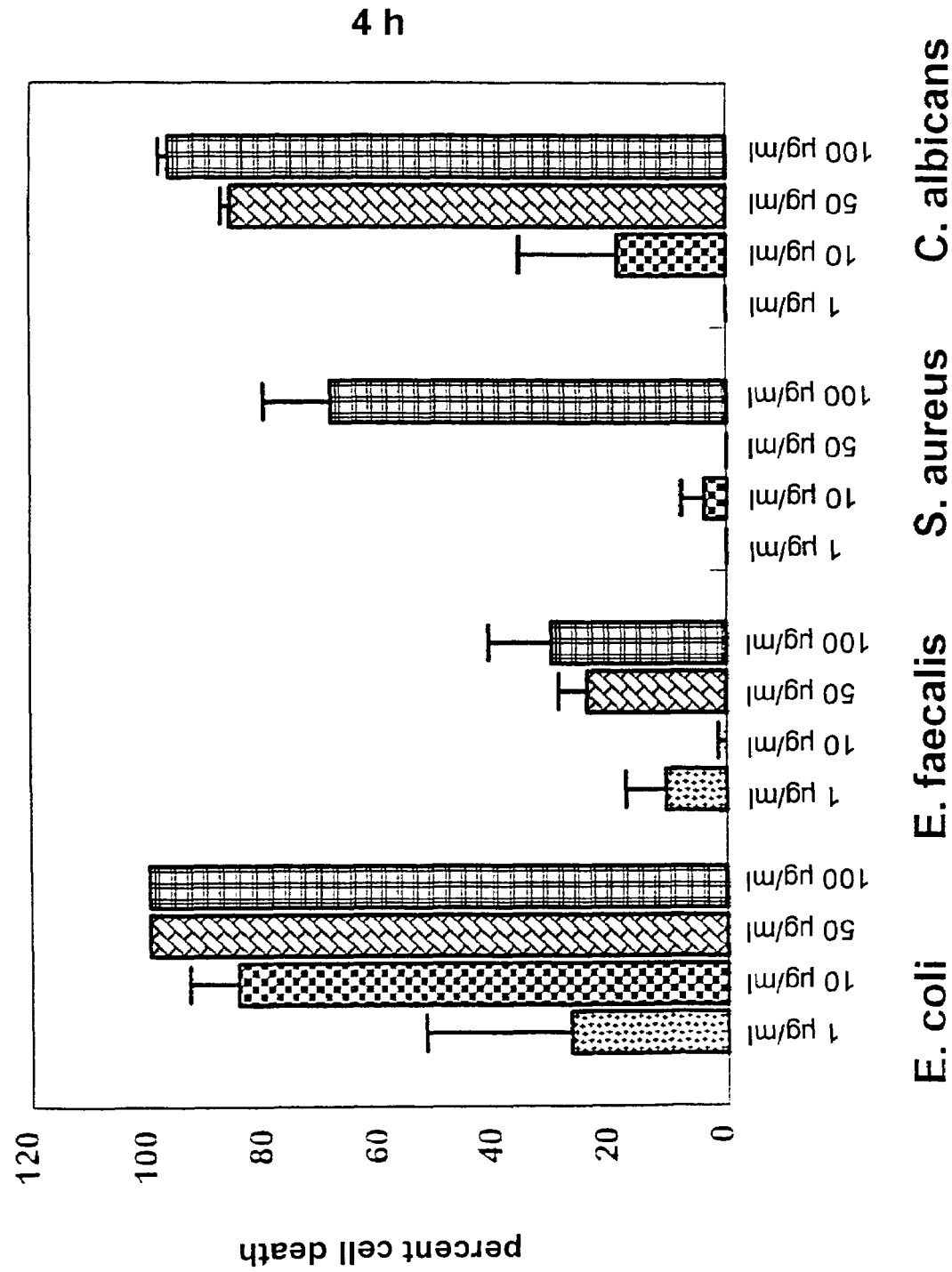
FIG. 3 in a bar diagram and an experimental approach as in FIG. 2 the antimicrobial effect of the peptide of SEQ ID No: 2, four bars from left to right respectively correspond to an amount of 1, 10, 50 and 100 µg/ml of the peptide.

FIG. 3 shows the antimicrobial effect on the four pathogens mentioned by the peptide of SEQ ID No: 2 on incubation for 4 h, with the four bars from left to right respectively corresponding to an amount of 1, 10, 50 and 100 μg/ml.

Figure 4:
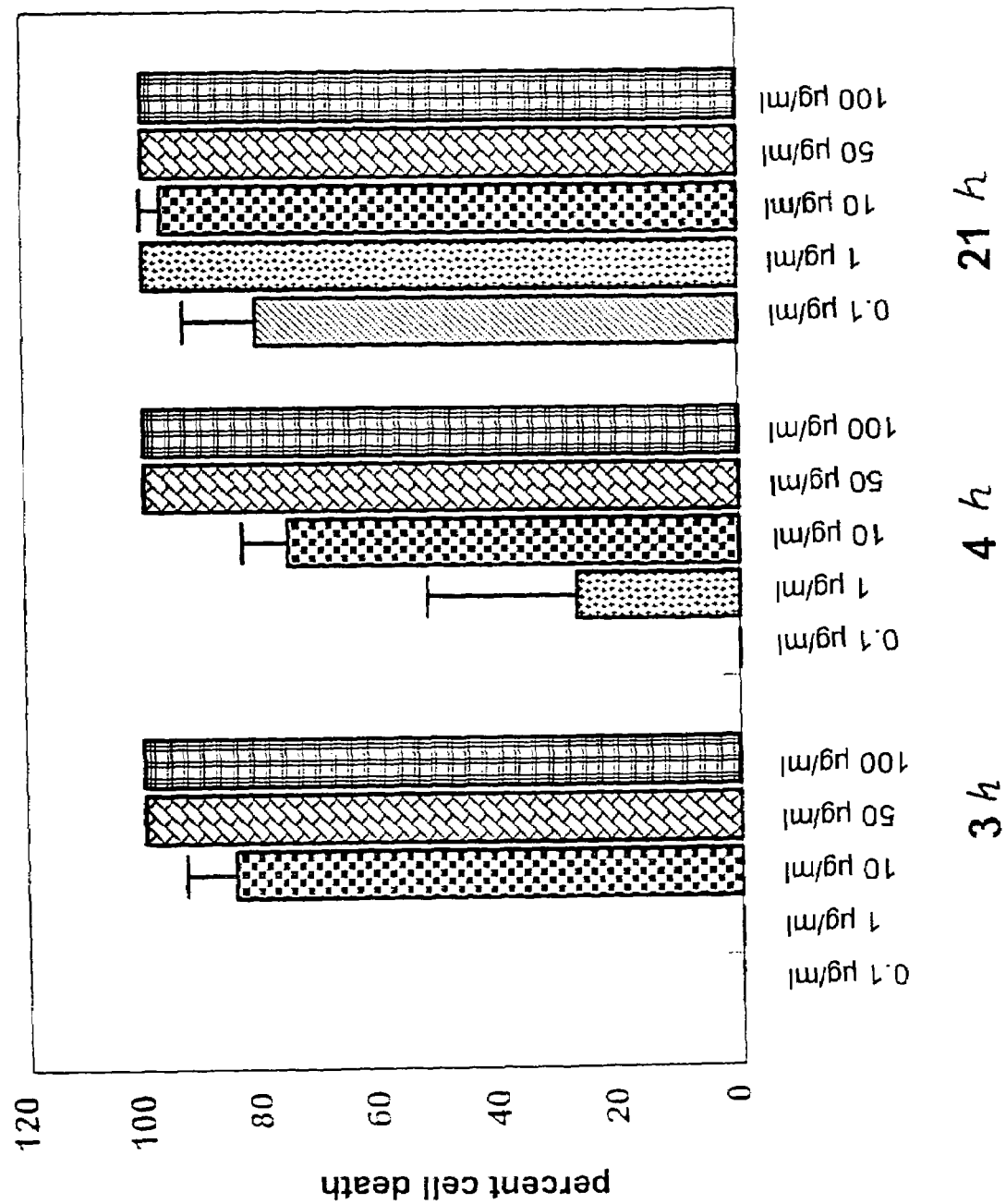
FIG. 4 in a bar diagram the quantity-dependent and incubation time-dependent antimicrobial effect of the peptide of SEQ ID No: 2 on *E. coli*, with the five bars from left to right respectively corresponding to an amount of 0.1, 1, 10, 50 and 100 µg/ml of the peptide.

FIG. 4 shows the time-dependent effect of the peptide of SEQ ID No: 2 on *E. coli*, with the five bars from left to right respectively corresponding to an amount of 0.1, 1, 10, 50 and 100 μg/ml.

Figure 5:
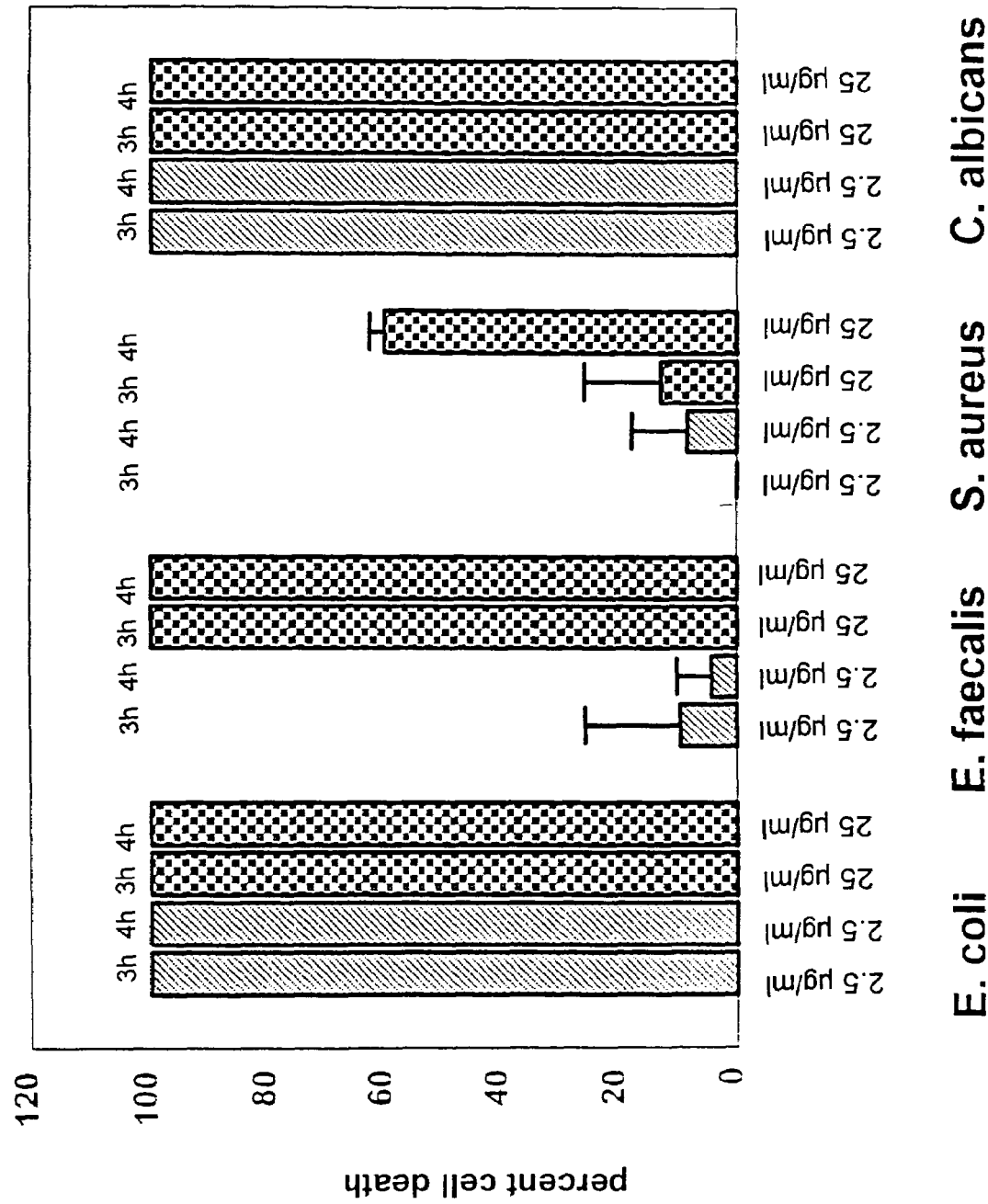
FIG. 5 in a bar diagram and an experimental approach as in FIG. 3 the antimicrobial effect of the peptide of SEQ ID No: 3. The two left-hand bars correspond in each case to an amount of 2.5 µg/ml and the two right-hand bars in a group correspond in each case to an amount of 25 µg/ml of peptide employed. The first and third bar in a group correspond in each case to an incubation time of 3 h, and the second and fourth bar in a group correspond in each case to an incubation time of 4 h.

Finally, FIG. 5 shows, comparably to FIG. 2, the antimicrobial effect of the peptide of SEQ ID No: 3 from the HPLC fraction on incubation for 3 h and 4 h. The two left-hand bars correspond in each case to an amount of 2.5 μg/ml and the two right-hand bars in a group correspond in each case to an amount of 25 μg/ml of peptide employed. The first and third bar in a group correspond in each case to an incubation time of 3 h, and the second and fourth bar in a group correspond in each case to an incubation time of 4 h.

It is evident from FIGS. 2 to 5 that all three tested peptides display a marked antimicrobial effect even when the amounts of peptide employed corresponds to the amount of DCD in sweat (1-10 μg/ml).

It is evident from the above that DCD and fragments of DCD display an antimicrobial effect on various pathogens, for example Gram-positive and Gram-negative bacteria, and yeasts. Since DCD and the fragments of DCD are secreted in sweat and, together with the latter, reach the surface of the skin, said peptides are particularly suitable for the curative or protective treatment of the skin because their natural site of action is evidently there.

---

What is claimed is:

1. An isolated antimicrobially active peptide of a dermcidin (DCD) protein consisting of SEQ ID NO: 2.

2. A pharmaceutical composition which comprises as active ingredient a peptide as claimed in claim 1 in an antimicrobially effective amount of 1 to 50 μg.

3. A cosmetic composition which comprises as active ingredient a peptide as claimed in claim 1 in an antimicrobially effective amount of 1 to 50 μg.

* * * * *